US 6,480,564 B1

(12) United States Patent
Kim et al.

(10) Patent No.: US 6,480,564 B1
(45) Date of Patent: Nov. 12, 2002

(54) SECTIONAL IMAGE PHOTOGRAPHY SYSTEM AND METHOD THEREOF

(75) Inventors: Chang-hyo Kim, Yongin (KR); Hyeong-cheol Kim, Sungnam (KR)

(73) Assignee: Samsung Electronics Co., Ltd., Suwon (KR)

( * ) Notice: Subject to any disclaimer, the term of this patent is extended or adjusted under 35 U.S.C. 154(b) by 0 days.

(21) Appl. No.: 09/496,623

(22) Filed: Feb. 2, 2000

(30) Foreign Application Priority Data

Feb. 2, 1999 (KR) .............................................. 99-3409

(51) Int. Cl.[7] .................................................. H05G 1/60
(52) U.S. Cl. ........................................... 378/21; 378/58
(58) Field of Search .......................... 378/58, 21, 98.8, 378/25

(56) References Cited

U.S. PATENT DOCUMENTS

| 4,926,452 A | | 5/1990 | Baker et al. |
| 5,388,136 A | * | 2/1995 | Halliday et al. ............... 378/58 |
| 5,594,768 A | * | 1/1997 | Fujii et al. ..................... 378/21 |
| 5,594,770 A | | 1/1997 | Bowles et al. |

FOREIGN PATENT DOCUMENTS

| JP | 3-51040 | 3/1991 |
| JP | 3-186710 | 8/1991 |
| JP | 4-326266 | 11/1992 |
| JP | 6-265487 | 9/1994 |

OTHER PUBLICATIONS

"Insite Tritech Gemini SIT (Silicon Intensified Target) Camera", Tritech International, (no date) 1 page.
N. E. Howard, "Image Intensifiers," OPSCI Application Note OAN–009, pp. 1–13, Feb. 19, 2002, www.opsci.com.

* cited by examiner

Primary Examiner—Robert H. Kim
Assistant Examiner—J. Yun
(74) Attorney, Agent, or Firm—Burns, Doane, Swecker & Mathis, L.L.P.

(57) ABSTRACT

A sectional image photography system includes a mounting table adapted to receive an object to be examined; a radiation projector for projecting a radiation toward an object being examined, the radiation being projected at a same level from different locations; a plane radiation detector for obtaining a plurality of partial radiation images formed from the radiations transmitted through the object in the form of electrical image signals; and an image processor for composition-processing the partial radiation images obtained by the plane radiation detector into a sectional image of a desired section of the object. Here, X-rays are used as the radiation. The plane radiation detector has a plurality of plane radiation detectors which are disposed to correspond to the radiation projected from different locations of the radiation projector. Accordingly, since the radiation images transmitted through the object are directly obtained by the plane radiation detectors, there is no radiation image distortion. Further, since there is no need to employ a driving mechanism, the structure of the product is simplified and the reliability is increased.

10 Claims, 7 Drawing Sheets

SECTIONAL IMAGE PHOTOGRAPHY SYSTEM AND METHOD THEREOF

BACKGROUND OF THE INVENTION

1. Field of the Invention

The present invention relates to a sectional image photography system and method thereof for examining an inner portion of an examined object which can not be seen with the naked eye, by obtaining a sectional image of the examined object.

2. Description of the Related Art

Generally, quality inspections are carried out with respect to mass-produced products to check possible abnormalities of the products. With respect to the object whose abnormality can not be checked with the naked eye such as soldered parts of electronic components mounted on a printed circuit board, for example, the quality inspection is carried out through a radiation sectional image such as an X-ray sectional image (hereinafter commonly called X-ray sectional image). The quality inspection through the X-ray sectional image is carried out by a sectional image photography system shown in FIG. 1, which is a special-purpose machine for the quality inspection.

Figure 1:
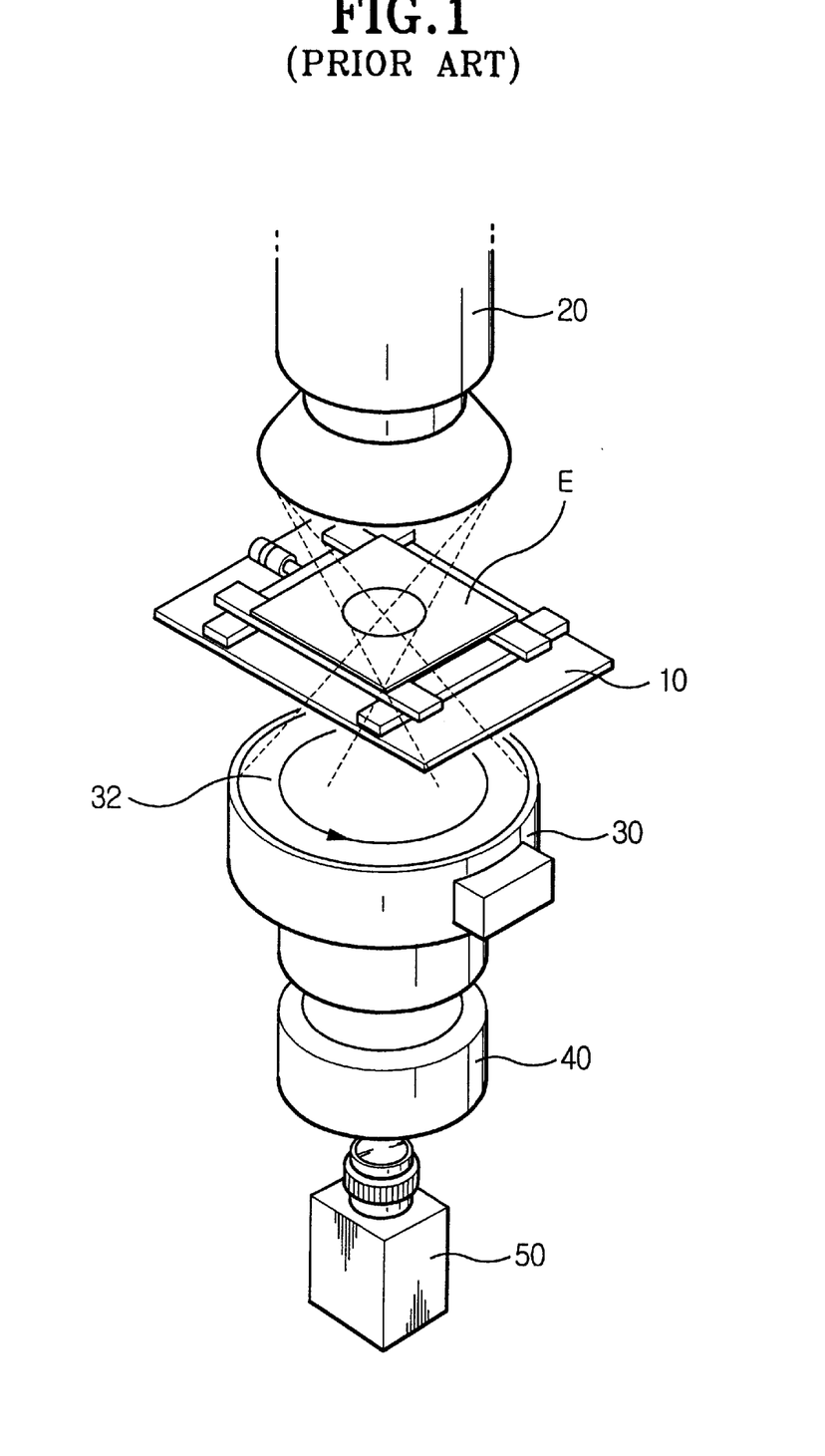
FIG. 1 is a perspective view for showing the structure of a conventional sectional image photography system.
Figure 2:
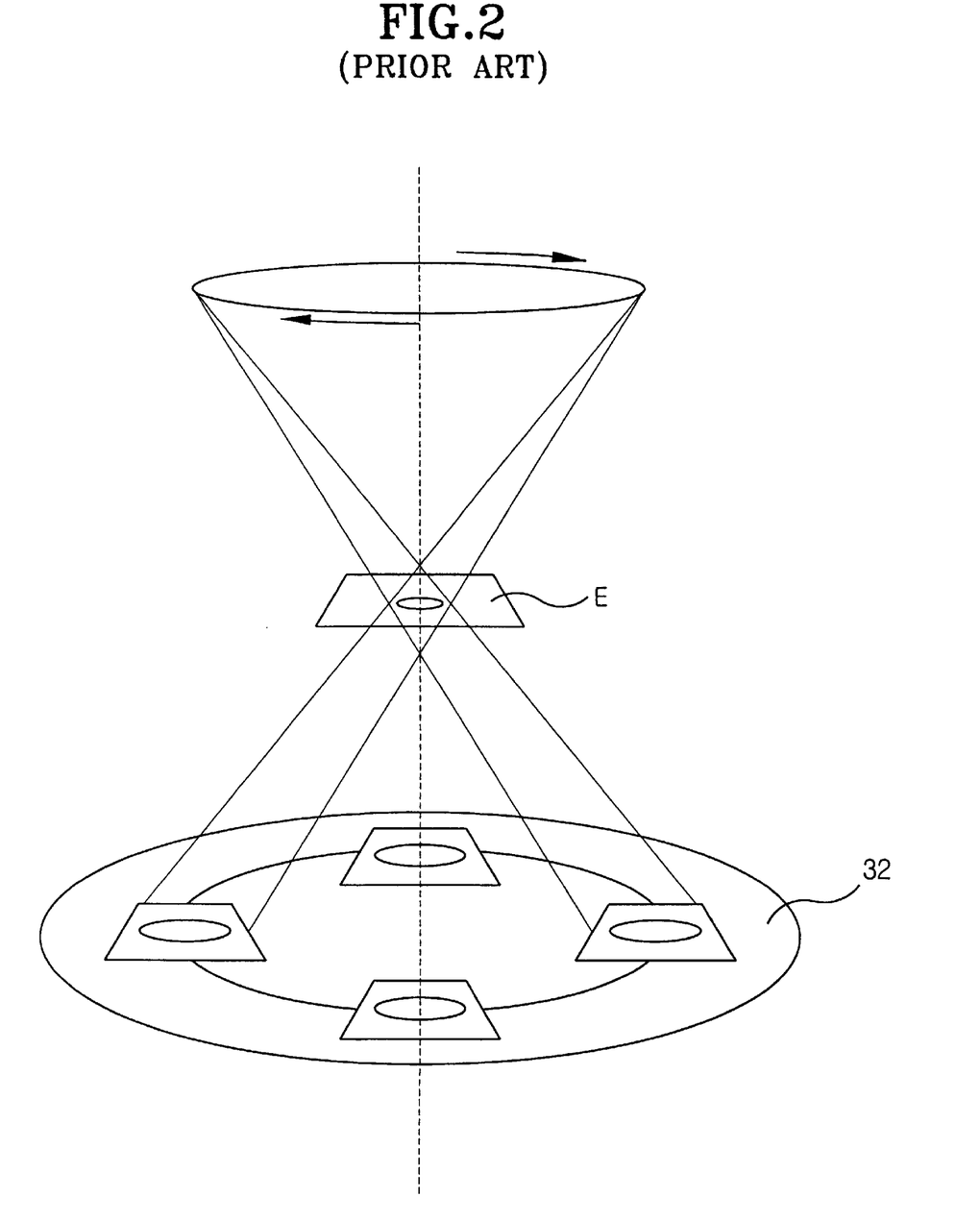
FIG. 2 is a view for showing transmitted image formative locations varying in accordance with the X-ray projecting directions in the conventional sectional image photography system shown in FIG. 1.

As shown in FIG. 1, the such a conventional system includes a mounting table 10, an X-ray projector 20, an image multiplying tube 30, a view selector 40, and a camera 50. As shown in FIG. 2, the X-rays are projected from the X-ray projector 20 rotatably along a circumference of the X-ray projector 20 at a constant speed. The X-rays are then transmitted through an examined object E which is loaded on the mounting table 10. The X-rays are transmitted through the examined object E into visible images on the image multiplying tube 30.

Here, as shown in FIG. 2, the partial images are formed on different locations on an image surface 32 of the image multiplying tube 30 in accordance with the respective X-ray projecting locations. The partial images on the respective locations are the result of the X-rays which are projected and transmitted from different directions, and by combining these partial images with a certain method, an X-ray sectional image of an arbitrary section of the examined object E is obtained.

Since the X-rays are rotatably projected from the X-ray projector 20 along the circumference thereof, the partial images are also rotatably formed on the image surface 32 of the image multiplying tube 30 in a circumferential direction. Accordingly, the view selector 40 selects the partial image on the image surface 32, and the camera 50 obtains the partial images.

Here, the view selector 40 guides the image formed on a certain location on the image surface 32 to the camera 50 by using a pair of mirrors, and the typical examples thereof are disclosed in the U.S. Pat. No. 4,926,452 granted to Baker et al. and assigned to the Four PI Systems Corporation, and the U.S. Pat. No. 5,594,770 granted to Bowles et al. and assigned to the ThermoSpectra Corporation.

Figure 3:
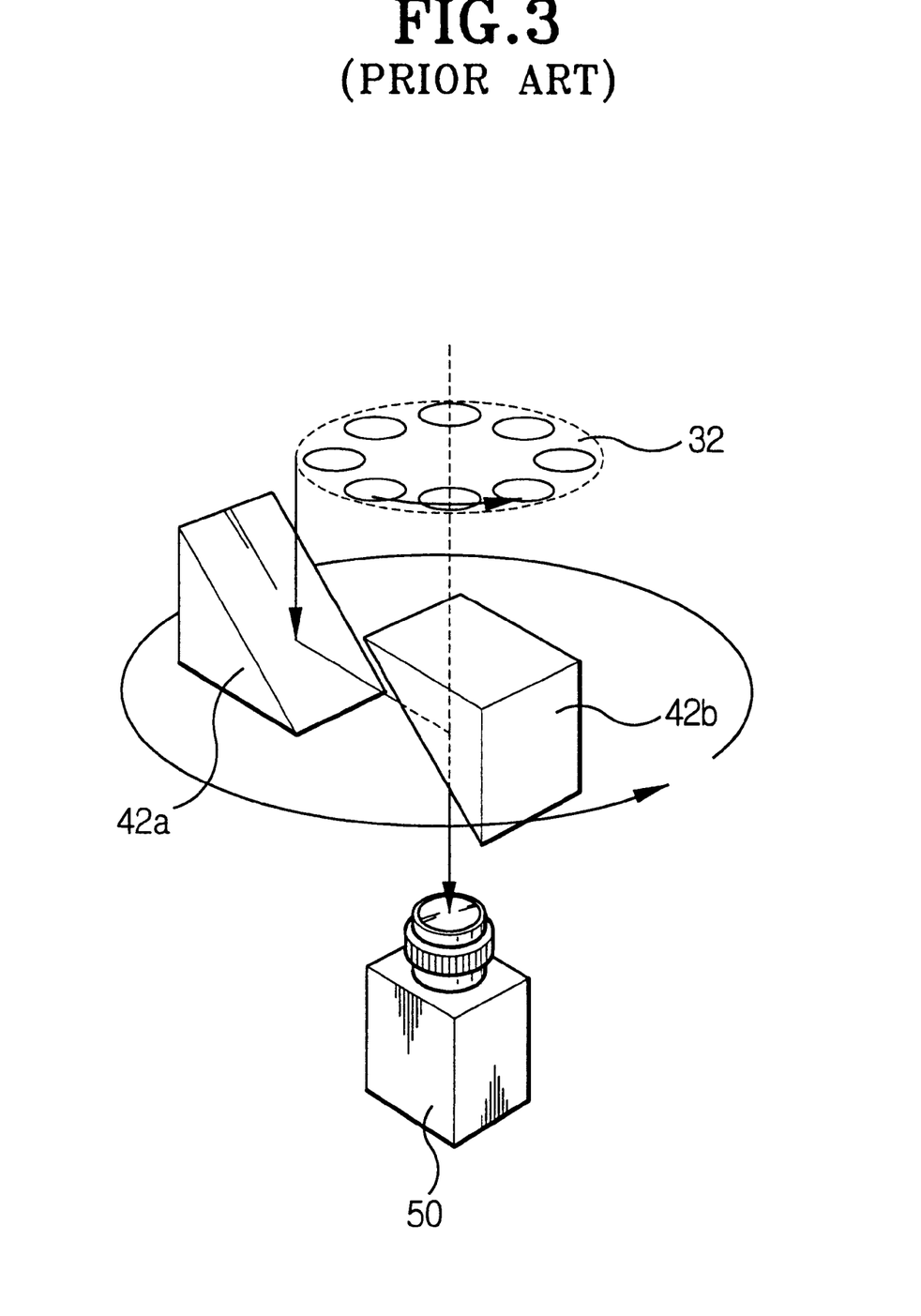
FIG. 3 is a schematic view of one example of a view selector employed in the conventional sectional image photography system.
Figure 4:
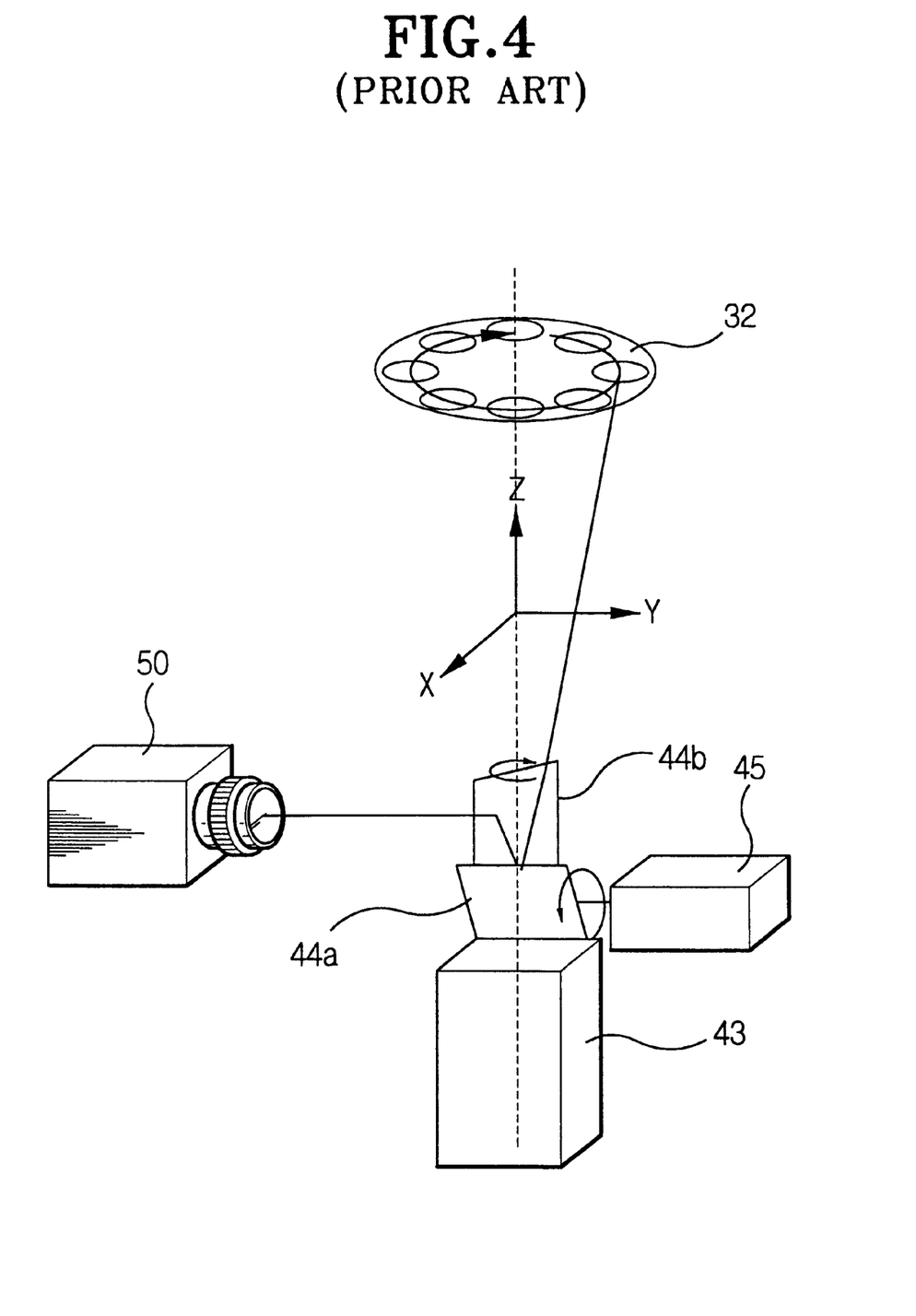
FIG. 4 is a schematic view of another example of a view selector employed in the conventional sectional image photography system.

According to the view selector of the U.S. Pat. No. 4,926,452, as shown in FIG. 3, a pair of slanted mirrors 42a and 42b are opposed to each other to transmit the image on the image surface 32 to the camera 50, while being rotated at the same speed with the images which are sequentially formed on the image surface 32 along the circumference of the image surface 32. According to the ThermoSpectra Corporation, as shown in FIG. 4, a pair of mirrors 44a and 44b are disposed under the image multiplying tube 30 to be rotated about X and Y axes, respectively. As the partial images are sequentially formed on the respective locations on the image surface 32, the pair of mirrors 44a and 44b are rotated about X and Y axes so as to select the partial image in a certain area on the image surface 32. Accordingly, the partial images on the image surface 32 are reflected against the pair of mirrors 44a and 44b sequentially, and obtained in the camera 50. Meanwhile, in FIG. 4, the reference numerals 43 and 45 refer to motors for rotating the pair of mirrors 44a and 44b.

The structure of the conventional sectional image photography system that uses the image multiplying tube 30 in a manner that a plurality of partial images formed on the image multiplying tube 30 are selected by the view selector 40 and then obtained by the camera 50, however, results in a disadvantage of having an image distortion according to the respective X-ray image formative locations on the image multiplying tube 30. Further, the view selector of the U.S. Pat. No. 5,594,770 has more serious distortion since an incident angle of optical axis is varied in accordance with the image formative locations.

If the image distortion is occurred, the clear sectional image of the examined object can not be obtained. Accordingly, there is a process of compensating the distortion of the image by a separate software before combining the partial images obtained by the camera 50, hindering accurate controlling of the sectional image photography system.

In addition to the disadvantage of image distortion mentioned above, the conventional system also has a disadvantage of having complex structure and high possibility of mechanical troubles since the conventional system employs a driving part for driving the view selector, i.e., a pair of mirrors 42', 44' and 42", 44" for selecting a plurality of partial images formed on the image surface of the image multiplying tube 30.

SUMMARY OF THE INVENTION

The present invention has been developed to overcome the above-mentioned problem of the related art, and accordingly, it is an object of the present invention to provide a sectional image photography system and method thereof capable of preventing a distortion of an X-ray image transmitted through an examined object.

Another object of the present invention is to provide a sectional image photography system and method thereof requiring a reduced number of parts, thus, having a simplified structure and an improved reliability.

The above object is accomplished by a sectional image photography system, according to the present invention, including: a mounting table adapted to receive an object to be examined; a radiation projector for projecting a radiation toward an object being examined, the radiation being projected at a same level from different locations; a plane radiation detector for obtaining a plurality of partial radiation images formed from the radiations transmitted through the object in the form of electrical image signals; and an image processor for composition-processing the partial radiation images obtained by the plane radiation detector into a sectional image of a desired section of the object.

According to the preferred embodiment of the present invention, the radiation is an X-ray.

The plane radiation detector may includes one, or a plurality of plane radiation detectors. When the one plane radiation detector is employed, the one plane radiation detector is mounted on an XY table and is moved to correspond to the image formative locations of the radiation images of the radiations projected from the respective locations of the radiation projector and are transmitted through the object. When the plurality of plane radiation detectors are employed, the plane radiation detectors are disposed to correspond to the radiation projected from different locations of the radiation projector. It is preferable that a number of the plane radiation detectors ranges from 4 to 8. More preferably, one more plane radiation detector is vertically disposed below the mounting table.

The image processor includes: a computer; and a frame grabber for converting image signals obtained by the plane radiation detector into image data which can be processed by the computer, and for inputting the image data into the computer.

Meanwhile, the above object is accomplished by a method for obtaining sectional image by using a sectional image photography system according to the present invention, including the steps of: a) placing an object to be examined on a mounting table of the sectional image photography system, and focusing a certain section of the object at a certain height at a focus surface of the sectional image photography system; b) projecting radiations generated from a radiation projector with respect to the object from at least two locations on a circumference of the radiation projector; c) obtaining at least two radiation partial images transmitted through an object being examined in the form of electrical image signals by using a plane radiation detector; and d) obtaining the sectional image by processing at least two radiation image signals which are obtained by the plane radiation detector.

Accordingly, by using the plane X-ray detector to obtain the X-ray images formed from the X-rays transmitted through the examined object, there is no image distortion. Further, when using a plurality of plane X-ray detectors, the structure of the sectional image photography system is simplified while the reliability thereof is improved since there is no need to employ a separate driving part.

BRIEF DESCRIPTION OF THE DRAWINGS

The above objects and advantages will be more apparent by describing the present invention with reference to the accompanied reference drawings, in which.

DETAILED DESCRIPTION OF THE PREFERRED EMBODIMENTS

Hereinafter, the preferred embodiments of the present invention will be described in greater detail with reference to the drawings accompanied.

Figure 5:
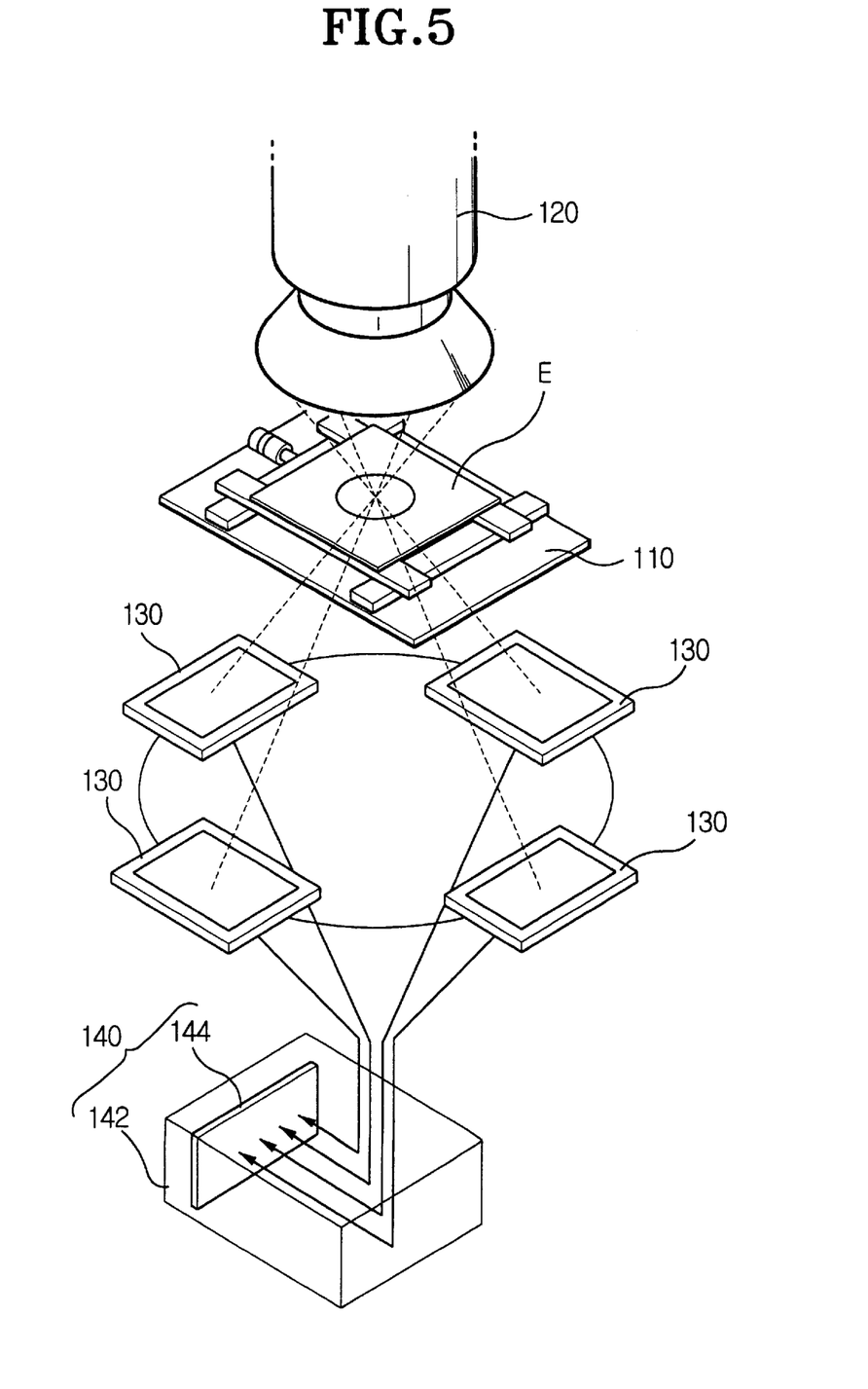
FIG. 5 is a schematic view for showing the structure of a sectional image photography system according to a first preferred embodiment of the present invention.

A sectional image photography system according to a first preferred embodiment of the present invention is shown in FIG. 5.

As shown in FIG. 5, the sectional image photography system according to the present invention includes a mounting table 110, a radiation projector 120, a plurality of plane radiation detectors 130, and an image processor 140.

The mounting table 110 on which an examined object E is loaded, is movable forward and backward, leftward and rightward, and upward and downward for obtaining a sectional image of a user's desired section of the examined object E. Then, by moving the mounting table 110, a section of the examined object E at a certain height is focused at a focus surface of the sectional image photography system.

The radiation projector 120 projects the radiations to the examined object E from different locations above the examined object E at the same level. Here, it is preferable that the X-rays are used as the radiation, and the radiation projecting locations usually form a circle.

A plurality of plane radiation detectors 130 are arranged in a circle under the mounting table 110 at the same level with one another. The plane radiation detectors 130 obtain and output the partial images of a plurality of radiations transmitted through the examined object E in the form of electrical image signals. As for the plane radiation detectors 130, there are various kinds of plane radiation detector 130 available, and this embodiment employs a model name 'FlashScan 30' made by French Corporation the Dpix. The kind of plane radiation detector, however, is not strictly limited, but can be any one available.

Figure 6:
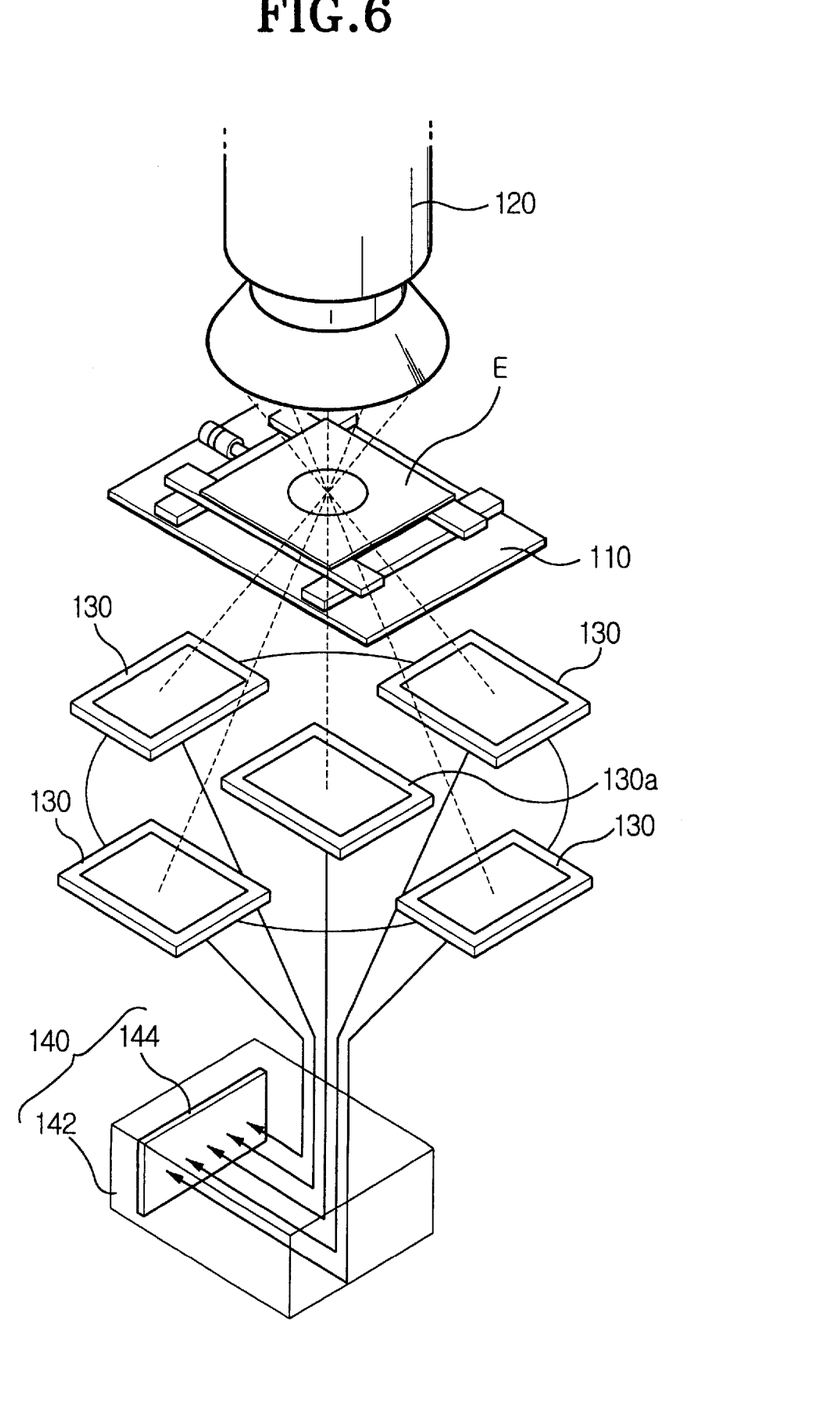
FIG. 6 is a schematic view for showing a construction of a sectional image photography system according to a second preferred embodiment of the present invention.

Meanwhile, although this embodiment employs four (4) plane radiation detectors 130 disposed in the circumferential direction of the radiation projector 120 approximately at 90° (degree), it is not strictly limited thereto. A greater number of plane radiation detectors 130 results in more precise contouring of the sectional image, but with increased product price and inspecting time. Accordingly, there is a need for limiting the number of radiation detectors 130 properly, and according to the experiment, it is preferable that the number of plane radiation detectors 130 ranges from 4 to 8. It is more preferable, as shown in FIG. 6, that an additional plane radiation detector 130a be vertically disposed below the mounting table 110 to obtain the radiation images which are vertically transmitted through the examined object E from the radiation projector 120.

The image processor 140 obtains the sectional image of the desired section of the examined object E by composition-processing the partial images obtained from the plurality of plane radiation detectors 130. The image processor 140 includes a frame grabber 144 and a computer 142. The frame grabber 144 converts the electric signals from the plane radiation detectors 130 into image data which can be processed by the computer 142, and inputs the image data into the computer 142. The computer 142 processes the image data, directly.

A method for obtaining sectional image by using the sectional image photography system according to the preferred embodiment of the present invention will be described below step by step.

First, a user places the object E to be examined on the mounting table 110 and fixes the same. Then, the user focuses a certain section at a certain height of the object E at the focus surface of the sectional image photography system by moving the mounting table 110. The above may be performed automatically, or by the user, manually.

After focusing the certain section of the object E, the radiation is projected from the radiation projector 120 with respect to the object E being examined, from at least 2 locations, and from 4 to 8 locations according to this preferred embodiment, on the circumference of the radiation projector 120.

When the radiations are projected from the radiation projector 120, and transmitted through the object E, to be formed on any one of a plurality of plane radiation detectors 130 and 130a, the plane radiation detectors 130 and 130a convert the image into the electrical image signal, and the electrical image signals are inputted to the frame grabber 144. The frame grabber 144 converts the electrical image signal into the image data which can be processed by the computer 142, and outputs the image data into the computer 142.

Accordingly, as the radiations are sequentially projected from the different locations of the radiation projector 120, the radiation images are sequentially and repetitiously formed on the plane radiation detectors 130 and 130a which are positioned to correspond to the respective radiation images. Here, the radiation images obtained by the plane radiation detectors 130 and 130a have higher quality since the same have almost no distortion when compared with the images obtained by the conventional image multiplying tube. Accordingly, the image distortion compensating process, which is conventionally included, can be omitted.

When the radiation images obtained from the respective plane radiation detectors 130 and 130a are inputted into the computer 142 via the frame grabber 144, the computer 142 composition-processes the plurality of images into a sectional image of desired section of the examined object E.

Figure 7:
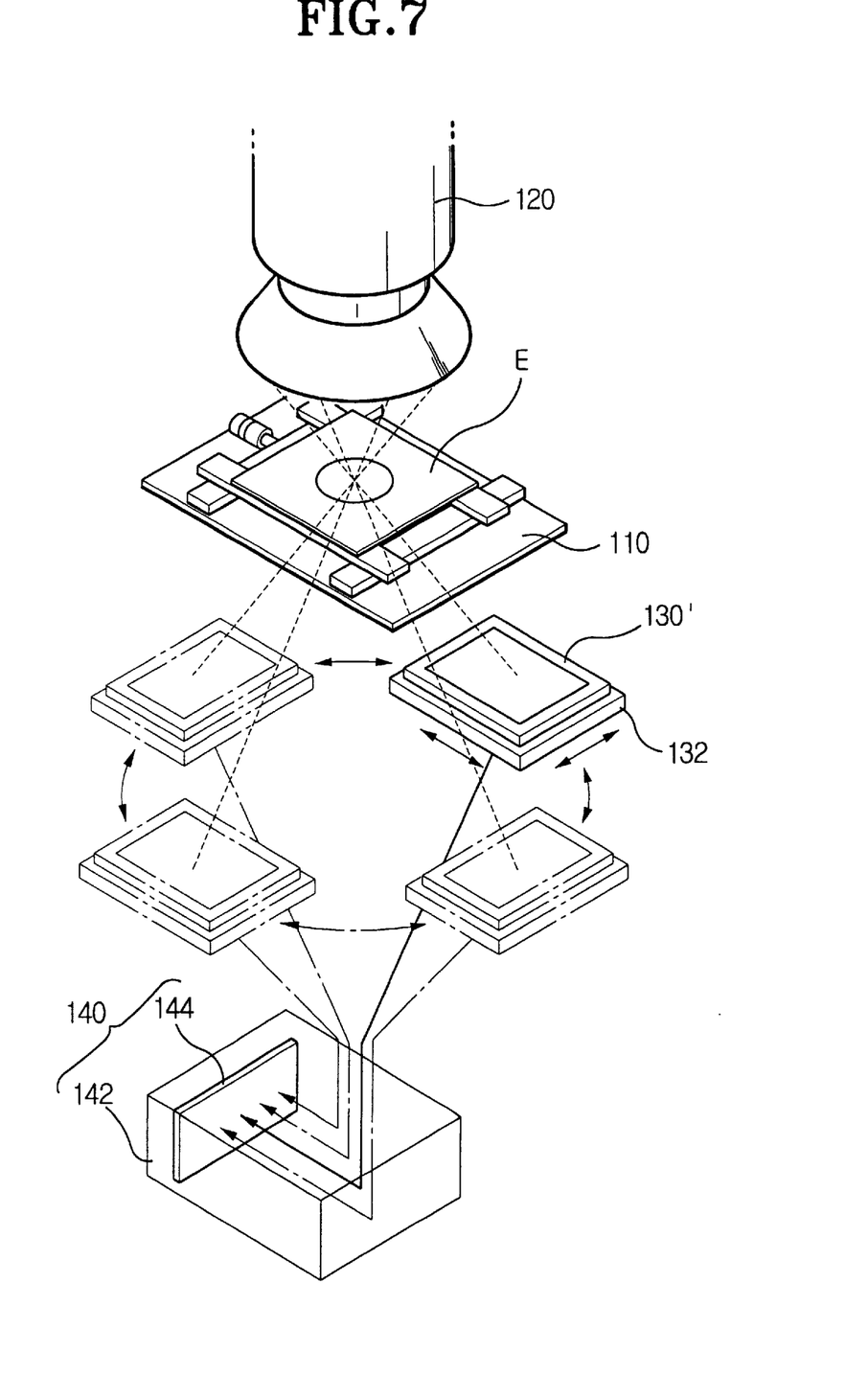
FIG. 7 is a schematic view of the structure of a sectional image photography system according to a third preferred embodiment of the present invention.

Meanwhile, instead of employing the plurality of plane x-ray detectors 130 and 130a, only one plane radiation detector 130' may be employed as shown in FIG. 7. In this other preferred embodiment, the structure is almost identical with the structure of the first preferred embodiment except for the fact that the plane radiation detector 130' is mounted on an XY table 132 and is sequentially moved to the locations corresponding to the radiation images projected from different locations of the radiation projector 120 by the movement of the XY table 132. Thus, the plane radiation detector 130' is driven by the XY table 132. Here, with respect to the structure and operation of the other preferred embodiment that are identical with the structure and operation of the first preferred embodiment described above, the further detailed description will be omitted.

As described above, in the sectional image photography system according to the present invention, unlike the conventional one, since the radiation image transmitted through the object E to be examined is directly obtained by using the plane radiation detector, there is no image distortion. Accordingly, the image distortion compensating process, which is inevitably included in the sectional image photographing process before the image composition process, can be omitted, and the sectional image photography system can be easily controlled.

Further, according to the present invention, since there is no need to employ the components such as the image multiplying tube, the view selector, and the camera, etc., the structure of the sectional image photography system is simplified, while the reliability thereof increased. These advantages are further increased when employing a plurality of plane radiation detectors, since there is no need for the driving part.

While the present invention has been particularly shown and described with reference to the preferred embodiment thereof, it will be understood by those skilled in the art that various changes in form and details may be effected therein without departing from the spirit and scope of the invention as defined by the appended claims.

What is claimed is:

1. A sectional image photography system comprising:
   a mounting table adapted to receive an object to be examined;
   a radiation projector for projecting a radiation toward an object being examined, the radiation being projected at a same portion of said object at a same level from different locations;
   a flat-type plane radiation detector for obtaining a plurality of partial radiation images formed from the radiation transmitted through a same portion of the object at a same level from different locations while the object remains stationary relative to the radiation projector, in the form of electrical image signals; and
   an image processor for composition-processing the partial radiation images obtained by the plane radiation detector into a sectional image of a desired section of the object.

2. The sectional image photography system as claimed in claim 1, wherein the radiation is X-ray radiation.

3. The sectional image photography system as claimed in claim 1, wherein said plane radiation detector is one plane radiation detector moved to correspond to the image formative locations of the radiation images of the radiations projected from the respective locations of the radiation projector and are transmitted through the object.

4. The sectional image photography system as claimed in claim 1, wherein the image processor comprises:
   a computer for composition-processing a plurality of radiation partial images obtained by the plane radiation detector; and
   a frame grabber for converting image signals obtained by the plane radiation detector into image data which can be processed by the computer, and for inputting the image data into the computer.

5. The sectional image photography system as claimed in claim 1, wherein said plane radiation detector obtains a plurality of partial radiation images formed from the radiation transmitted through a same portion of the object at a same level from different locations while the object remains stationary relative to the radiation projector and the plane radiation detector, in the form of electrical image signals.

6. A sectional image photography system comprising:
   a mounting table adapted to receive an object to be examined;
   a radiation projector for projecting a radiation toward an object being examined, the radiation being projected at a same portion of said object at a same level from different locations;
   a plurality of plane radiation detectors, which are disposed to correspond to the radiation projected from different locations of the radiation projector through a same portion of said object at said same level, for obtaining a plurality of partial radiation images formed from the radiation transmitted through a same portion of the object at a same level from different locations, in the form of electrical image signals; and an image processor for composition-processing the partial radiation images obtained by the plane radiation detector into a sectional image of a desired section of the object.

7. The sectional image photography system as claimed in claim 6, wherein a number of the plane radiation detectors ranges from 4 to 8.

8. A sectional image photography system comprising:
- a mounting table adapted to receive an object to be examined;
- a radiation projector for projecting a radiation toward an object being examined, the radiation being projected at a same portion of said object at a same level from different locations;
- a flat-type plane radiation detector for obtaining a plurality of partial radiation images formed from the radiation transmitted through a same portion of the object at a same level from different locations while the object remains stationary relative to the radiation projector, in the form of electrical image signals;
- an image processor for composition-processing the partial radiation images obtained by the plane radiation detector into a sectional image of a desired section of the object; and
- a plane radiation detector vertically disposed below the mounting table.

9. A method for obtaining a sectional image by using a sectional image photography system comprising the steps of:
- a) placing an object to be examined on a mounting table of the sectional image photography system, and focusing a certain section of the object at a certain height at a focus surface of the sectional image photography system;
- b) projecting radiation generated from a radiation projector with respect to an object being examined from at least two locations on a circumference of the radiation projector;
- c) obtaining at least two radiation partial images transmitted through the object from said at least two locations in the form of electrical image signals by using a flat-type plane radiation detector while the object is stationary relative to the radiation projector; and
- d) obtaining the sectional image by processing at least two radiation image signals which are obtained by the plane radiation detector.

10. The sectional image photography method as claimed in claim 9, wherein the step of obtaining at least two radiation portion images transmitted through the object occurs whole the object is stationary relative to the radiation projector and the plane radiation detector.

* * * * *